(12) United States Patent
Van Epps et al.

(10) Patent No.: US 10,765,501 B2
(45) Date of Patent: Sep. 8, 2020

(54) DUAL PLANE BREAST IMPLANT

(71) Applicant: Allergan, Inc., Irvine, CA (US)

(72) Inventors: Dennis E. Van Epps, Goleta, CA (US); David J. Schuessler, Santa Ana, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 15/819,544

(22) Filed: Nov. 21, 2017

(65) Prior Publication Data

US 2018/0092726 A1    Apr. 5, 2018

Related U.S. Application Data

(63) Continuation of application No. 14/728,249, filed on Jun. 2, 2015, now Pat. No. 9,848,972, which is a continuation of application No. 13/908,232, filed on Jun. 3, 2013, now Pat. No. 9,050,184, which is a continuation-in-part of application No. 12/540,317, filed on Aug. 12, 2009, now Pat. No. 8,506,627.

(60) Provisional application No. 61/655,937, filed on Jun. 5, 2012, provisional application No. 61/088,418, filed on Aug. 13, 2008.

(51) Int. Cl.
*A61F 2/12* (2006.01)
*A61F 2/00* (2006.01)
*A61F 2/30* (2006.01)

(52) U.S. Cl.
CPC .............. *A61F 2/0077* (2013.01); *A61F 2/12* (2013.01); *A61F 2002/0081* (2013.01); *A61F 2002/0086* (2013.01); *A61F 2002/30322* (2013.01); *A61F 2250/0026* (2013.01); *A61F 2250/0051* (2013.01)

(58) Field of Classification Search
CPC ...................................................... A61F 2/12
See application file for complete search history.

(56) References Cited

U.S. PATENT DOCUMENTS

| | | | |
|---|---|---|---|
| 2,324,735 A | 7/1943 | Spanel |
| 2,762,476 A | 9/1956 | Barnett |
| 2,805,208 A | 9/1957 | Roche |
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,600,718 A | 8/1971 | Boone |
| 3,665,520 A | 5/1972 | Perras et al. |

(Continued)

FOREIGN PATENT DOCUMENTS

| | | |
|---|---|---|
| CA | 2049377 | 3/1992 |
| CA | 2811975 | 11/2011 |

(Continued)

OTHER PUBLICATIONS

Alvarez, Sonia et al, Synthesis of Macro/Mesoporous Silica and Carbon Monoliths by Using a Commercial Polyurethane Foam as Sacrificial Template, Material Letters, 2007, 2378-2381, 61.

(Continued)

*Primary Examiner* — Seema Mathew
(74) *Attorney, Agent, or Firm* — Nathan S. Smith; Sujohn Das; Morgan, Lewis & Bockius LLP

(57) ABSTRACT

A soft breast prosthesis is provided, the prosthesis having a surface configuration advantageous for dual plane placement of the prosthesis in a breast.

20 Claims, 9 Drawing Sheets

(56) References Cited

U.S. PATENT DOCUMENTS

| | | |
|---|---|---|
| 3,700,380 A | 10/1972 | Kitrilakis |
| 3,852,832 A | 12/1974 | McGhan et al. |
| 3,934,274 A | 1/1976 | Hartley |
| 4,034,751 A | 7/1977 | Hung |
| 4,157,085 A | 6/1979 | Austad |
| 4,231,979 A | 11/1980 | White et al. |
| 4,237,237 A | 12/1980 | Jarre et al. |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein et al. |
| 4,499,211 A | 2/1985 | Walch et al. |
| 4,531,244 A | 7/1985 | Hamas |
| 4,533,568 A | 8/1985 | McClinton et al. |
| 4,573,999 A | 3/1986 | Netto |
| 4,584,324 A | 4/1986 | Bauman et al. |
| 4,592,755 A | 6/1986 | Penton et al. |
| 4,608,396 A | 8/1986 | Bauman et al. |
| 4,610,690 A | 9/1986 | Tiffany |
| 4,636,213 A | 1/1987 | Pakiam |
| 4,643,733 A | 2/1987 | Becker |
| 4,647,618 A | 3/1987 | Bauman et al. |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Ebert et al. |
| 4,740,208 A | 4/1988 | Cavon |
| 4,772,285 A | 9/1988 | Ksander et al. |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl et al. |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki et al. |
| 4,859,383 A | 8/1989 | Dillon |
| 4,859,712 A | 8/1989 | Cox |
| 4,889,744 A * | 12/1989 | Quaid ................. A61F 2/0077 427/2.24 |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox |
| 4,950,292 A | 8/1990 | Audretsch |
| 4,955,907 A | 9/1990 | Ledergerber |
| 4,955,909 A | 9/1990 | Ersek et al. |
| 4,960,425 A * | 10/1990 | Yan ........................ A61F 2/12 623/8 |
| 4,963,150 A | 10/1990 | Brauman |
| 4,965,430 A | 10/1990 | Curtis et al. |
| 4,969,899 A | 11/1990 | Cox |
| 5,002,572 A | 3/1991 | Picha |
| 5,007,929 A * | 4/1991 | Quaid ................. A61F 2/0077 623/8 |
| 5,007,940 A | 4/1991 | Berg |
| 5,011,494 A | 4/1991 | von Recum et al. |
| 5,022,942 A | 6/1991 | Yan et al. |
| 5,026,394 A | 6/1991 | Baker |
| 5,034,422 A | 7/1991 | Triolo et al. |
| 5,035,249 A | 7/1991 | Sasaki et al. |
| 5,092,348 A | 3/1992 | Dubrul et al. |
| 5,092,882 A | 3/1992 | Lynn et al. |
| 5,104,409 A | 4/1992 | Baker |
| 5,116,370 A | 5/1992 | Foglietti |
| 5,116,387 A | 5/1992 | Berg |
| 5,128,088 A | 7/1992 | Shimomura et al. |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,204,024 A | 4/1993 | Onaka et al. |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,282,856 A | 2/1994 | Ledergerber |
| 5,296,069 A | 3/1994 | Robert |
| 5,340,656 A | 8/1994 | Sachs et al. |
| 5,348,788 A | 9/1994 | White |
| 5,354,338 A | 10/1994 | Ledergerber |
| 5,356,429 A | 10/1994 | Seare |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle et al. |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iversen et al. |
| 5,534,023 A | 7/1996 | Henley |
| 5,545,217 A | 8/1996 | Offray |
| 5,545,220 A | 8/1996 | Andrews et al. |
| 5,549,671 A | 8/1996 | Waybright et al. |
| 5,571,179 A | 11/1996 | Manders |
| RE35,391 E | 12/1996 | Brauman |
| 5,589,176 A | 12/1996 | Seare, Jr. |
| 5,605,693 A | 2/1997 | Seare |
| 5,607,473 A | 3/1997 | Weber-Unger |
| 5,624,674 A | 4/1997 | Seare |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle |
| 5,674,285 A | 10/1997 | Quaid |
| 5,681,572 A | 10/1997 | Seare |
| 5,776,159 A | 7/1998 | Young |
| 5,779,734 A | 7/1998 | Ledergerber |
| 5,798,065 A | 8/1998 | Picha |
| 5,824,081 A * | 10/1998 | Knapp ...................... A61F 2/12 623/23.72 |
| 5,843,189 A | 12/1998 | Perouse |
| 5,855,588 A | 1/1999 | Young |
| 5,871,497 A | 2/1999 | Young |
| 5,895,423 A | 4/1999 | Becker et al. |
| 5,935,164 A | 8/1999 | Iverson |
| 5,961,552 A | 10/1999 | Iversen et al. |
| 5,964,803 A | 10/1999 | Iversen et al. |
| 5,965,076 A | 10/1999 | Banks |
| 5,984,943 A | 11/1999 | Young |
| 5,993,716 A | 11/1999 | Draenert |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. et al. |
| 6,214,926 B1 | 4/2001 | Winn |
| 6,232,374 B1 | 5/2001 | Liu et al. |
| 6,315,796 B1 | 11/2001 | Eaton |
| 6,340,648 B1 | 1/2002 | Imura et al. |
| 6,387,133 B1 | 5/2002 | Perouse |
| 6,432,138 B1 | 8/2002 | Offray |

(56) References Cited

U.S. PATENT DOCUMENTS

| | | |
|---|---|---|
| 6,464,726 B1 | 10/2002 | Heljenek |
| 6,520,989 B1 | 2/2003 | Eaton |
| 6,531,523 B1 | 3/2003 | Davankov |
| 6,544,287 B1 | 4/2003 | Johnson et al. |
| 6,602,452 B2 | 8/2003 | Schuessler |
| 6,605,116 B2 | 8/2003 | Falcon |
| 6,638,308 B2 | 10/2003 | Corbitt et al. |
| 6,673,285 B2 | 1/2004 | Ma |
| 6,692,527 B1 | 2/2004 | Bellin et al. |
| 6,743,254 B2 | 6/2004 | Guest et al. |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Mattew Turner |
| 6,881,226 B2 | 4/2005 | Corbitt |
| 6,900,055 B1 | 5/2005 | Fuller et al. |
| 6,913,626 B2 | 7/2005 | McGhan |
| 6,916,339 B1 | 7/2005 | Missana |
| 6,921,418 B2 | 7/2005 | Ledergerber |
| 6,932,840 B1 | 8/2005 | Bretz |
| 6,993,406 B1 | 1/2006 | Cesarano, III |
| 7,081,135 B2 | 7/2006 | Smith |
| 7,081,136 B1 | 7/2006 | Becker |
| 7,105,116 B2 | 9/2006 | Bellin et al. |
| 7,169,180 B2 | 1/2007 | Brennan |
| 7,192,450 B2 | 3/2007 | Brauker |
| 7,244,270 B2 | 7/2007 | Lesh |
| 7,268,169 B2 | 9/2007 | Hirayma et al. |
| 7,309,232 B2 | 12/2007 | Rutherford et al. |
| 7,323,208 B2 | 1/2008 | Ma |
| 7,476,249 B2 | 1/2009 | Frank |
| 7,520,896 B2 | 4/2009 | Benslimane |
| 7,547,393 B2 | 6/2009 | Ramaswamy |
| 7,625,405 B2 | 12/2009 | Purkait |
| 7,632,228 B2 | 12/2009 | Brauker |
| 7,632,291 B2 | 12/2009 | Stephens et al. |
| 7,641,688 B2 | 1/2010 | Lesh |
| 7,645,475 B2 | 1/2010 | Prewett |
| 7,758,788 B2 | 7/2010 | Job |
| 7,867,061 B2 | 1/2011 | Elshout |
| 8,202,317 B2 | 6/2012 | Becker |
| 8,221,494 B2 | 7/2012 | Schreck et al. |
| 8,313,527 B2 | 11/2012 | Powell et al. |
| 8,409,279 B2 | 4/2013 | Freund |
| 8,425,600 B2 * | 4/2013 | Maxwell .............. A61L 27/50 623/8 |
| 8,487,012 B2 | 7/2013 | Goraltchouk et al. |
| 8,506,627 B2 | 8/2013 | Van Epps et al. |
| 8,546,458 B2 | 10/2013 | Thompson et al. |
| 8,556,968 B2 | 10/2013 | Hamas et al. |
| 8,562,677 B2 | 10/2013 | Job |
| 8,679,279 B2 | 3/2014 | Thompson et al. |
| 8,685,296 B2 | 4/2014 | Liu et al. |
| 8,728,159 B2 | 5/2014 | Kim |
| 8,765,039 B1 | 7/2014 | Ledergerber |
| 8,801,782 B2 | 8/2014 | Nofrey et al. |
| 8,877,822 B2 | 11/2014 | Liu et al. |
| D723,162 S | 2/2015 | Brogan et al. |
| 9,011,333 B2 | 4/2015 | Geissler et al. |
| 9,044,897 B2 | 6/2015 | Manesis et al. |
| 9,050,184 B2 | 6/2015 | Van Epps |
| 9,155,613 B2 | 10/2015 | Thompson et al. |
| 9,205,238 B2 | 12/2015 | Ledergerber |
| 9,205,577 B2 | 12/2015 | Liu et al. |
| 9,593,224 B2 | 3/2017 | Liu et al. |
| 9,673,516 B2 | 6/2017 | Mejia |
| 9,688,006 B2 | 6/2017 | Nieto et al. |
| 9,750,600 B2 | 9/2017 | Mayo |
| 9,901,438 B2 | 2/2018 | Mejia et al. |
| 10,111,744 B2 | 10/2018 | Mora et al. |
| 10,176,412 B2 | 1/2019 | Geissler et al. |
| 2001/0010024 A1 | 7/2001 | Ledergerber |
| 2002/0038147 A1 | 3/2002 | Miller |
| 2002/0062154 A1 | 5/2002 | Ayers |
| 2002/0143396 A1 | 10/2002 | Falcon et al. |
| 2002/0193885 A1 | 12/2002 | Legeay et al. |
| 2003/0036803 A1 | 2/2003 | McGhan |
| 2003/0093151 A1 | 5/2003 | Zhang |
| 2003/0105469 A1 | 6/2003 | Karmon |
| 2003/0129717 A1 | 7/2003 | Becker et al. |
| 2003/0205846 A1 | 11/2003 | Bellin et al. |
| 2003/0208269 A1 | 11/2003 | Eaton |
| 2004/0010225 A1 | 1/2004 | Schuessler |
| 2004/0115241 A1 | 6/2004 | Calhoun et al. |
| 2004/0127985 A1 | 7/2004 | Bellin et al. |
| 2004/0137032 A1 | 7/2004 | Wang |
| 2004/0143327 A1 | 7/2004 | Ku |
| 2004/0148024 A1 | 7/2004 | Williams |
| 2004/0153151 A1 | 8/2004 | de Vincente |
| 2004/0176493 A1 | 9/2004 | Ferguson |
| 2004/0213986 A1 | 10/2004 | Kim et al. |
| 2005/0055093 A1 | 3/2005 | Brennan |
| 2005/0070124 A1 | 3/2005 | Miller et al. |
| 2005/0112169 A1 | 5/2005 | Brauker et al. |
| 2005/0122169 A1 | 6/2005 | Watanabe |
| 2005/0175702 A1 | 8/2005 | Muller-Schulte |
| 2005/0196452 A1 | 9/2005 | Boyan et al. |
| 2005/0216094 A1 * | 9/2005 | Prewett ............... A61F 2/0077 623/23.74 |
| 2005/0251083 A1 | 11/2005 | Carr-Brendel et al. |
| 2006/0002810 A1 | 1/2006 | Grohowski |
| 2006/0030939 A1 * | 2/2006 | Frank ..................... A61F 2/12 623/8 |
| 2006/0036266 A1 | 2/2006 | Sulamanidze et al. |
| 2006/0036320 A1 * | 2/2006 | Job ........................ A61F 2/12 623/8 |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2006/0247761 A1 | 11/2006 | Greenberg et al. |
| 2006/0257377 A1 | 11/2006 | Atala et al. |
| 2007/0038310 A1 | 2/2007 | Guetty |
| 2007/0088434 A1 * | 4/2007 | Frank ..................... A61F 2/12 623/8 |
| 2007/0093911 A1 | 4/2007 | Fricke et al. |
| 2007/0104693 A1 | 5/2007 | Quijano et al. |
| 2007/0104695 A1 | 5/2007 | Quijano et al. |
| 2007/0116735 A1 | 5/2007 | Calhoun et al. |
| 2007/0135916 A1 | 6/2007 | Maxwell et al. |
| 2007/0154525 A1 | 7/2007 | Calhoun et al. |
| 2007/0190108 A1 | 8/2007 | Datta et al. |
| 2007/0198085 A1 | 8/2007 | Benslimane |
| 2008/0009830 A1 | 1/2008 | Fujimoto et al. |
| 2008/0071371 A1 | 3/2008 | Elshout |
| 2008/0075752 A1 | 3/2008 | Ratner et al. |
| 2008/0095823 A1 | 4/2008 | Williams et al. |
| 2008/0154366 A1 | 6/2008 | Frank |
| 2008/0241212 A1 | 10/2008 | Moses et al. |
| 2008/0268019 A1 | 10/2008 | Badylak et al. |
| 2008/0312739 A1 | 12/2008 | Agerup et al. |
| 2009/0043377 A1 | 2/2009 | Greenberg et al. |
| 2009/0045166 A1 | 2/2009 | Li |
| 2009/0082864 A1 | 3/2009 | Chen et al. |
| 2009/0087641 A1 | 4/2009 | Favis et al. |
| 2009/0093878 A1 | 4/2009 | Glicksman |
| 2009/0118829 A1 | 5/2009 | Powell et al. |
| 2009/0125107 A1 | 5/2009 | Maxwell |
| 2009/0148829 A1 | 6/2009 | Ecker et al. |
| 2009/0169716 A1 | 7/2009 | Linhardt et al. |
| 2009/0198331 A1 | 8/2009 | Kesten et al. |
| 2009/0198332 A1 | 8/2009 | Becker |
| 2009/0198333 A1 | 8/2009 | Becker |
| 2009/0254179 A1 | 10/2009 | Burnett |
| 2010/0042211 A1 | 2/2010 | Van Epps et al. |
| 2010/0075056 A1 | 3/2010 | Axisa et al. |
| 2010/0121429 A1 | 5/2010 | Greenan et al. |
| 2010/0268327 A1 | 10/2010 | Bruszewski et al. |
| 2010/0292790 A1 | 11/2010 | Stroumpoulis et al. |
| 2011/0035004 A1 | 2/2011 | Maxwell |
| 2011/0054605 A1 | 3/2011 | Becker |
| 2011/0093069 A1 | 4/2011 | Goraltchouk et al. |

(56) References Cited

U.S. PATENT DOCUMENTS

| | | |
|---|---|---|
| 2011/0106249 A1 | 5/2011 | Becker |
| 2011/0117267 A1 | 5/2011 | Powell et al. |
| 2011/0172798 A1 | 7/2011 | Staiger |
| 2011/0184531 A1 | 7/2011 | Goraltchouk et al. |
| 2011/0196488 A1 | 8/2011 | Goraltchouk et al. |
| 2011/0196489 A1 | 8/2011 | Van Epps et al. |
| 2011/0257623 A1 | 10/2011 | Marshall et al. |
| 2011/0270378 A1 | 11/2011 | Bruszewski et al. |
| 2011/0276133 A1 | 11/2011 | Liu et al. |
| 2011/0276134 A1 | 11/2011 | Manesis et al. |
| 2011/0278755 A1 | 11/2011 | Liu et al. |
| 2011/0282444 A1 | 11/2011 | Liu et al. |
| 2011/0301693 A1 | 12/2011 | Hartley et al. |
| 2011/0309541 A1 | 12/2011 | Thompson et al. |
| 2011/0313073 A1 | 12/2011 | Goraltchouk et al. |
| 2011/0313504 A1 | 12/2011 | Golding et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077012 A1 | 3/2012 | Liu et al. |
| 2012/0077891 A1 | 3/2012 | Liu et al. |
| 2012/0101574 A1 | 4/2012 | Goraltchouk et al. |
| 2012/0142798 A1 | 6/2012 | Thompson et al. |
| 2012/0165934 A1 | 6/2012 | Schuessler |
| 2012/0185041 A1 | 7/2012 | Mortarino et al. |
| 2012/0221105 A1 | 8/2012 | Altman et al. |
| 2012/0232652 A1 | 9/2012 | Mora et al. |
| 2012/0245685 A1 | 9/2012 | Yu |
| 2012/0271401 A1 | 10/2012 | Bruszewski et al. |
| 2012/0277858 A1 | 11/2012 | Brinon |
| 2012/0321777 A1 | 12/2012 | Stroumpoulis et al. |
| 2013/0013062 A1 | 1/2013 | Thompson et al. |
| 2013/0023987 A1 | 1/2013 | Liu et al. |
| 2013/0032962 A1 | 2/2013 | Liu et al. |
| 2013/0034633 A1 | 2/2013 | von Hassein |
| 2013/0053956 A1 | 2/2013 | Powell et al. |
| 2013/0158657 A1 | 6/2013 | Nofrey et al. |
| 2013/0178699 A1 | 7/2013 | Saint et al. |
| 2013/0209661 A1 | 8/2013 | Goraltchouk et al. |
| 2013/0245148 A1 | 9/2013 | Thompson et al. |
| 2013/0253645 A1* | 9/2013 | Kerr .................. A61F 2/0063 623/8 |
| 2013/0261745 A1 | 10/2013 | Van Epps |
| 2013/0295379 A1 | 11/2013 | Goraltchouk et al. |
| 2013/0302511 A1 | 11/2013 | Goraltchouk et al. |
| 2013/0310934 A1 | 11/2013 | Van Epps et al. |
| 2014/0005783 A1 | 1/2014 | Van Epps et al. |
| 2014/0039617 A1 | 2/2014 | Maxwell |
| 2014/0180412 A1* | 6/2014 | Nieto .................. A61F 2/12 623/8 |
| 2014/0277348 A1 | 9/2014 | Roeder |
| 2015/0282926 A1 | 10/2015 | Chacon et al. |
| 2016/0022866 A1 | 1/2016 | Liu et al. |
| 2016/0130690 A1 | 5/2016 | Winn et al. |
| 2016/0151542 A1 | 6/2016 | Liu et al. |
| 2016/0310262 A1* | 10/2016 | Doucet .................. A61F 2/12 |
| 2017/0049549 A1 | 2/2017 | Bayat et al. |
| 2017/0256850 A1 | 9/2017 | Mejia |
| 2017/0290652 A1 | 10/2017 | Nieto et al. |
| 2018/0200043 A1 | 7/2018 | Mejia et al. |
| 2018/0360594 A1 | 12/2018 | Schuessler et al. |
| 2019/0029807 A1 | 1/2019 | Nieto et al. |
| 2020/0100892 A1* | 4/2020 | Limem .................. A61F 2/12 |

FOREIGN PATENT DOCUMENTS

| | | |
|---|---|---|
| CA | 2975348 | 8/2015 |
| CA | 3007138 | 6/2017 |
| CA | 3013698 | 8/2017 |
| CA | 3019747 | 10/2017 |
| CA | 3020876 | 10/2017 |
| CA | 3023507 | 11/2017 |
| CN | 2587376 Y | 11/2003 |
| CN | 104837441 | 8/2015 |
| CN | 108697337 | 10/2018 |
| CN | 109069251 | 12/2018 |
| CN | 109152531 | 1/2019 |
| CN | 109152640 | 1/2019 |
| EP | 0230672 A1 | 8/1987 |
| EP | 0293256 A1 | 11/1988 |
| EP | 0315814 A2 | 5/1989 |
| EP | 332371 | 9/1989 |
| EP | 0419134 | 3/1991 |
| EP | 0522585 A1 | 1/1993 |
| EP | 710468 | 5/1996 |
| EP | 1532942 A1 | 5/2005 |
| EP | 1796595 | 6/2007 |
| EP | 1847369 B1 | 12/2008 |
| EP | 2446858 | 5/2012 |
| EP | 2568875 | 3/2013 |
| EP | 2895994 | 7/2015 |
| EP | 2921137 | 9/2015 |
| EP | 2931490 | 10/2015 |
| EP | 2962662 | 1/2016 |
| EP | 3107487 | 12/2016 |
| EP | 3383314 | 10/2018 |
| EP | 3413788 | 12/2018 |
| EP | 2895109 B1 | 1/2019 |
| EP | 3439543 | 2/2019 |
| EP | 3442468 | 2/2019 |
| EP | 3443933 | 2/2019 |
| EP | 2227175 B1 | 3/2019 |
| ES | 2409691 | 6/2013 |
| FR | 2840617 A1 | 12/2003 |
| GB | 1022736 | 3/1966 |
| GB | 2225016 | 5/1990 |
| JP | 2003-062062 | 4/2003 |
| JP | 2007-029717 | 8/2007 |
| KR | 20180103873 | 9/2018 |
| KR | 20180116302 | 10/2018 |
| KR | 20180134358 | 12/2018 |
| KR | 20180137503 | 12/2018 |
| KR | 20190008252 | 1/2019 |
| MX | 2012012801 A | 5/2014 |
| RU | 2340308 C1 | 12/2008 |
| WO | WO 90/14927 A1 | 12/1990 |
| WO | WO 97/15242 | 5/1997 |
| WO | 1998010803 A1 | 3/1998 |
| WO | WO 98/42318 | 10/1998 |
| WO | 2000024437 A2 | 5/2000 |
| WO | WO 00/56376 | 9/2000 |
| WO | 2004037318 A2 | 5/2004 |
| WO | 2004062531 A1 | 7/2004 |
| WO | WO 2005/020849 | 3/2005 |
| WO | 2006133366 A1 | 12/2006 |
| WO | WO 2008/001591 | 1/2008 |
| WO | 2009061672 A1 | 5/2009 |
| WO | 2009110917 A1 | 9/2009 |
| WO | 2010019292 A1 | 2/2010 |
| WO | 2010019761 A1 | 2/2010 |
| WO | 2010136840 A2 | 12/2010 |
| WO | WO 2011/066441 | 6/2011 |
| WO | 2011094155 A2 | 8/2011 |
| WO | 2011097499 A1 | 8/2011 |
| WO | WO 2011/143324 | 11/2011 |
| WO | 20130184569 A1 | 12/2013 |
| WO | WO 2014/043631 | 3/2014 |
| WO | WO 2014/047013 | 3/2014 |
| WO | WO 2014/076339 | 5/2014 |
| WO | WO 2015/121686 | 8/2015 |
| WO | WO 2017/093528 | 6/2017 |
| WO | WO 2017/137853 | 7/2017 |
| WO | WO 2017/175055 | 10/2017 |
| WO | WO 2017/181144 | 10/2017 |
| WO | WO 2017/184962 | 10/2017 |
| WO | WO 2017/196973 | 11/2017 |

(56) References Cited

FOREIGN PATENT DOCUMENTS

WO  WO 2018/078446   5/2018
WO  WO 2018/188930   10/2018

OTHER PUBLICATIONS

Barnsley, Philip et al., Textured Surface Breast Implants in the Prevention of Capsular Contracture Among Breast Augmentation Patients: A Meta-Analysis of Randomized Controlled Trials, Plastic and Reconstructive Surgery, 2006, 2182-2190, 117(7).
Barr, S. et al., Current Implant Surface Technology: An Examination of Their Nanostructure and Their Influence on Fibroblast Alignment and Biocompatibility, Elastic, 2009, 198-217, 9.
Brauker, James et al., Neovascularization of Synthetic Membranes Directed by Membrane Microarchitecture, Journal of Biomedical Materials Research, 1995, 1517-1524, 29, John Wiley & Sons, Inc.
Brohim, Robert et al., Early Tissue Reaction to Textured Breast Implant Surfaces, Annals of Plastic Surgery, Apr. 1992, 354-362, vol. 28, No. 4.
Inamed Aesthetics Brochure, Silicone-Filled Breast Implants, Directions for Use Style 410, 2003, 23 pages, www.inamedaesthetics.com.
Ma, Peter, Scaffolds for Tissue Fabrication, Materials Today, 2004, 30-40, 7.
Mikos, Antonius et al., Formation of Highly Porous Biodegradable Scaffolds for Tissue Engineering, Electronic Journal of Biotechnology, 2000, 114-119, 3(2).
Minami, Eliza, The Composition and Behavior of Capsules Around Smooth and Textured Breast Implants in Pigs, Plast. Reconstr. Surg., 2006, 874-884, 118.
Murphy, William L. et al., Salt Fusion: An Approach to Improve Pore Interconnectivity Within Tissue Engineering Scaffolds, Tissue Engineering, 2002, 43-52, 8 (1), US.
Sharkawy, Adam et al., Engineering the Tissue Which Encapsulates Subcutaneous Implants. II. Plasma-Tissue Exchange Properties, Journal of Biomedical Materials Research, 1998, 586-597, 40, John Wiley & Sons, Inc.
Wei, Guobao et al., Macroporous and Nanofibrous Polymer Scaffolds and Polymer/Bone-Like Apatite Composite Scaffolds Generated by Sugar Spheres, Journal of Biomedical Materials Research, 2006, 306-315, 78A.
Zhang, et al., Macroporous Alumina Monoliths Prepared by Filling Polymer Foams with Alumina Hydrogels, Journal of Materials Science, 2009, 931-938, 44, Springer Science.
Capes et al., "Fabrication of polymeric scaffolds with a controlled distribution of pores," J of Materials Science: Materials in Medicine, Dec. 2005, vol. 16, No. 12, DD 1069-1075.
Kim et al., "Modified release of coated sugar spheres using drug-containing polymeric dispersions," Archives Pharmacal Research, 2007, vol. 30, No. 1, pp. 124-130.
Nace, "A Surface Texture Modeling System for Solid Freeform Fabrication," Massachusetts Institute of Technology Sep. 1997.
Yu et al., "Softness measurement for open-cell foam materials and human soft tissue," Measurement Science and Technology, 2006, vol. 17, pp. 1785-1791.

\* cited by examiner

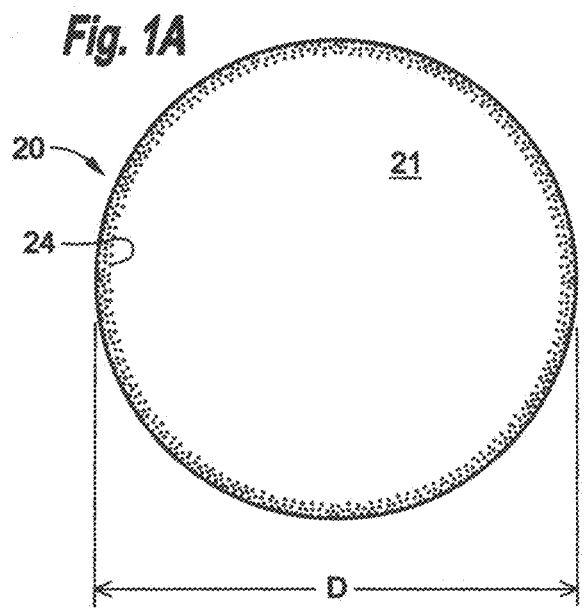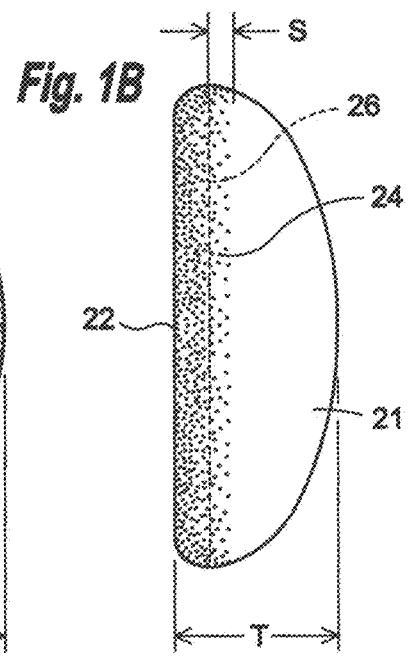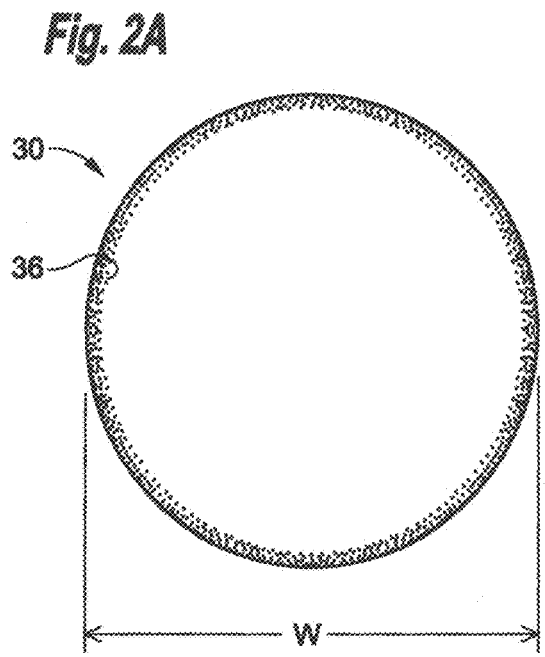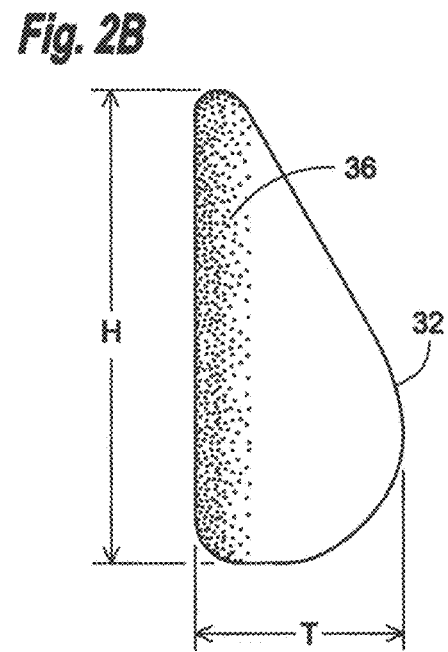

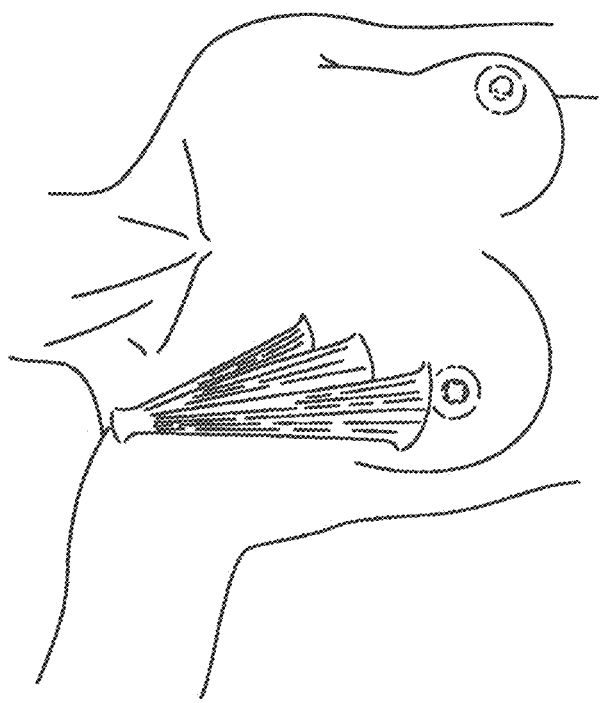
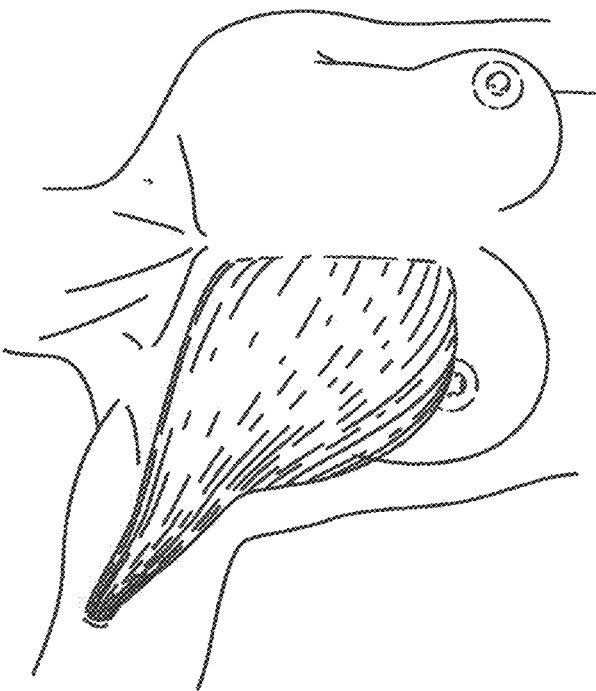

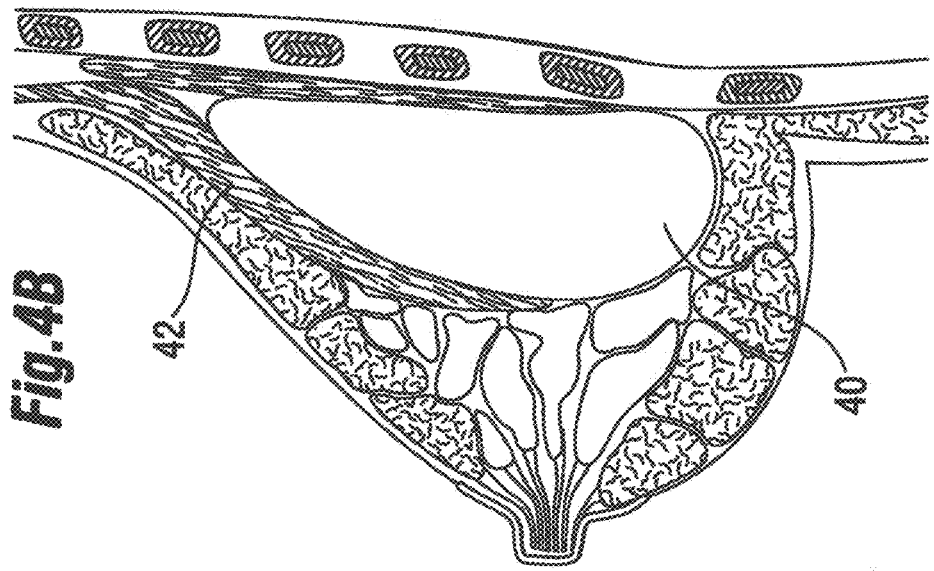
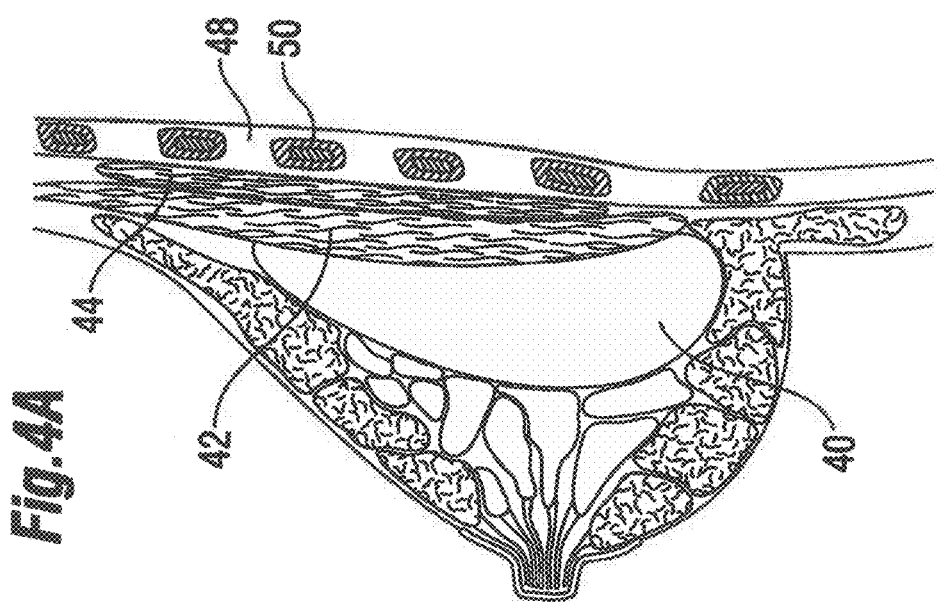

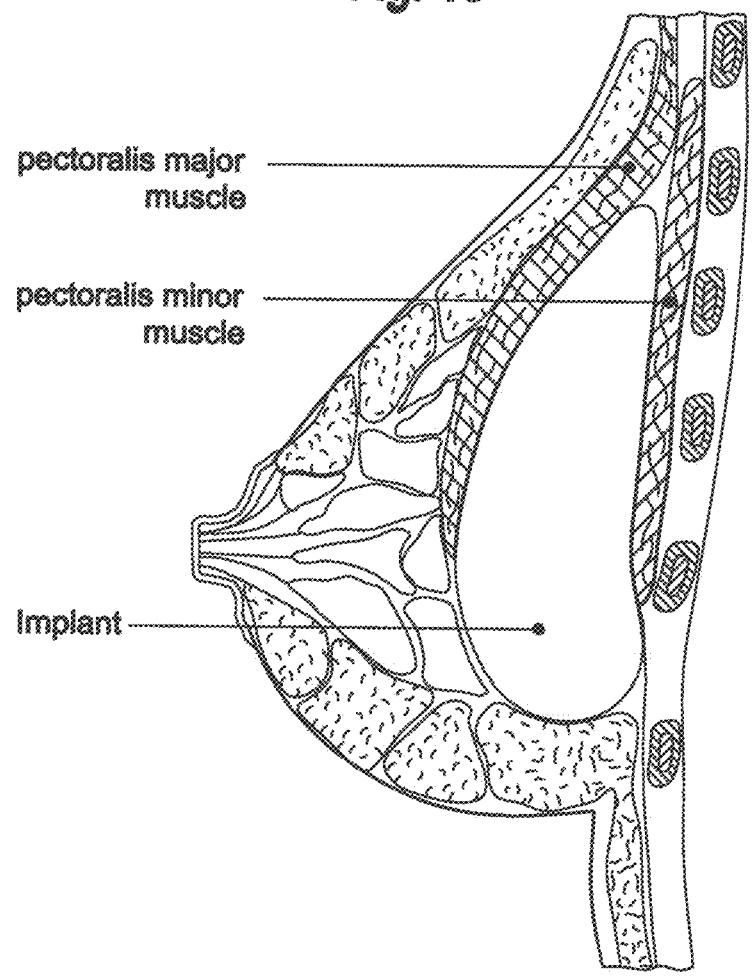

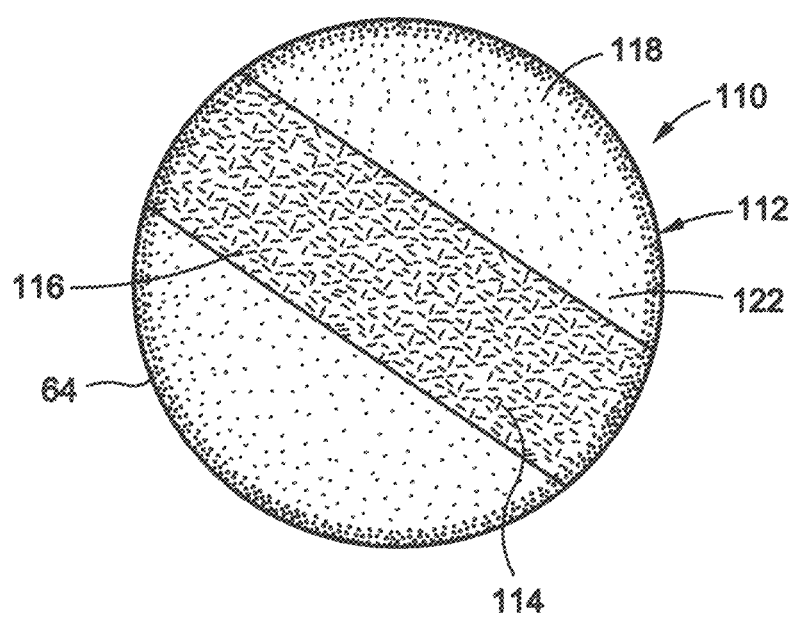

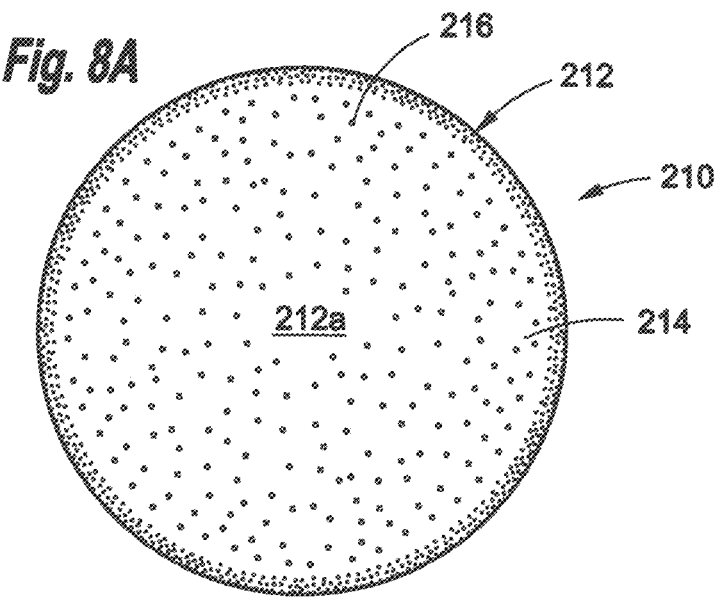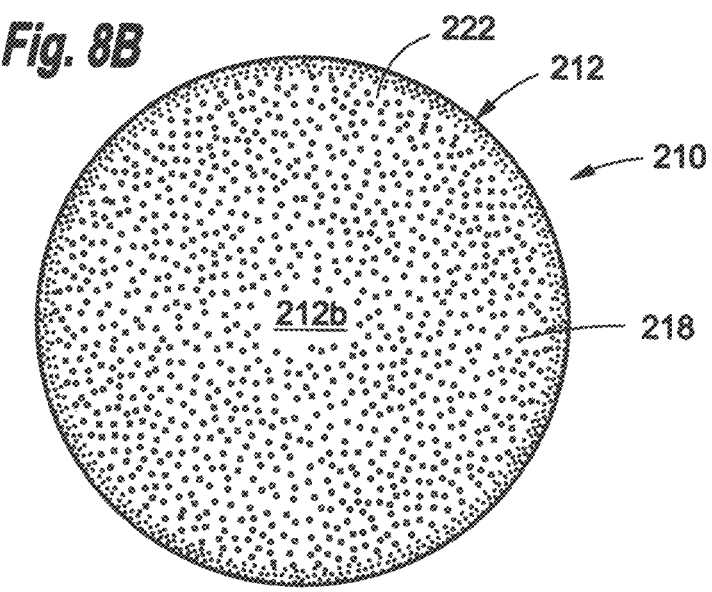

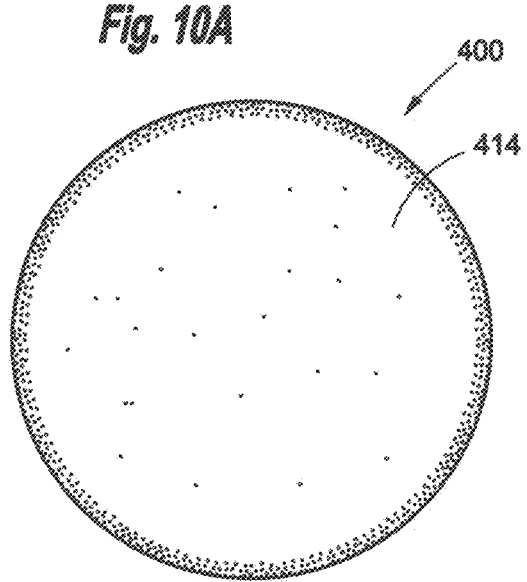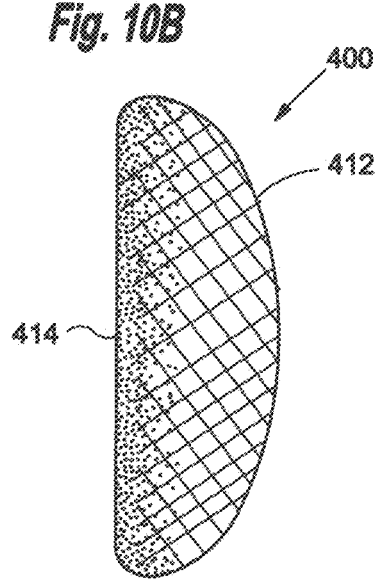

DUAL PLANE BREAST IMPLANT

CROSS REFERENCE TO RELATED APPLICATIONS

This application is a continuation of U.S. patent application Ser. No. 14/728,249 filed on Jun. 2, 2015, which is a continuation of U.S. patent application Ser. No. 13/908,232 filed Jun. 3, 2013, which claims priority to U.S. Provisional Patent Application No. 61/655,937, filed Jun. 5, 2012, and which U.S. patent application Ser. No. 13/908,232 is a continuation-in-part of U.S. patent application Ser. No. 12/540,317, filed Aug. 12, 2009 which claims priority to U.S. Provisional Patent Application No. 61/088,418, filed Aug. 13, 2008, the entire contents of each of these documents being incorporated herein by this reference.

FIELD OF THE INVENTION

The present invention relates to soft prosthetic implants and, more particularly, to textured exterior surfaces of such implants, for instance, breast implants.

BACKGROUND OF THE INVENTION

Implantable prostheses are commonly used to replace or augment body tissue. In the case of breast cancer, it is sometimes necessary to remove some or all of the mammary gland and surrounding tissue, which creates a void that can be filled with an implantable prosthesis. The implant serves to support surrounding tissue and to maintain the appearance of the body. The restoration of the normal appearance of the body has a beneficial psychological effect on post-operative patients, eliminating much of the shock and depression that often follows extensive surgical procedures. Implantable prostheses are also used more generally for restoring the normal appearance of soft tissue in various areas of the body, such as the buttocks, chin, calf, etc.

Soft implantable prostheses typically include a relatively thin and flexible envelope or shell made of vulcanized (cured) silicone elastomer. The shell is filled either with a silicone gel or with a normal saline solution. The filling of the shell takes place before or after the shell is inserted through an incision in the patient.

In the United States, women can generally choose between two different types of breast implant shell surfaces: a smooth surface and a textured surface. The surgeon generally recommends the type of surface based on his or her technique and the need of the individual patient.

Breast implants may be placed in the breast in one of several different positions, depending on desired outcome, and/or patient and surgeon preference.

In subglandular placement, the breast implant is placed in a surgically formed pocket directly between the glandular breast tissue and the pectoralis major muscle. This placement most approximates the plane of normal breast tissue. In addition, this placement may offer shorter surgery, less pain and discomfort and perhaps a faster recovery. On the downside, subglandular placement may result in a more palpable implant, a higher chance of visible rippling or folding of the implant, and higher risk of capsular contracture.

In submuscular placement, the breast implant is placed beneath the pectoralis major muscle. Thus, the implant is further away from the skin surface and may be less visible or less palpable. This placement may appear more "natural" because the implant is further away from the skin. It may require a longer surgery and recovery period, but is believed to results in a reduced chance for capsular contracture. In breast reconstruction patients where natural breast tissue may be substantially or entirely absent, this placement approach effects maximal coverage of the implant.

Dual plane breast implant placement is a combination approach in which the implant is placed beneath the pectoralis major muscle, after the surgeon releases the inferior muscular attachments. As a result, the upper portion of the implant is partially beneath the pectoralis major muscle, while the lower portion of the implant is positioned in the subglandular plane. This implantation technique may achieve improved coverage of the upper portion of the implant and allow filling of minor laxity of the lower breast.

Despite many advances in the development of safe and comfortable breast prostheses, there remains room for improvement.

SUMMARY OF THE INVENTION

The present invention provides a prosthesis suitable for implantation in a human being, for example, a breast implant suitable for use in reconstruction or augmentation of the human breast. The prosthesis generally comprises an implantable member, for example, an elastomeric shell that is filled or is fillable with a liquid or gel. The implantable member has an exterior surface including one or more fixation regions defined thereon and configured, positioned or structured to provide enhanced or controlled tissue ingrowth or adhesion.

In accordance with one aspect of the invention, the fixation surfaces are discrete, generally elongated surface portions extending across an anterior face or a posterior face of the implant. These fixation surfaces, sometimes herein referred to as "fixation regions", are generally defined by a texture, roughness or sheen that is different from a texture, roughness or sheen of adjacent surface portions of the implant.

In some embodiments, the fixation regions have an increased or enhanced texture relative to the balance of the anterior face or posterior face of the implant. In other words, the balance of the exterior surface may be relatively less textured than the fixation regions. In some embodiments, the fixation regions are textured and adjacent surfaces, for example, the surface or surfaces that are not defined by the fixation regions, are substantially less textured, or are relatively smooth.

The prosthesis may be structured to encourage enhanced tissue ingrowth or adhesion at the fixation regions, relative to an otherwise identical surface without such texture, roughness or sheen.

In one aspect of the invention, the fixation regions are positioned and/or configured such that the prosthesis, after implantation in the body, moves more naturally with the human body, for example, in relative unity with the muscles of the body. It is contemplated that because the implant moves more naturally with the human body, the implant may be less prone to wear resulting from material stresses relative to conventional implants, for example, implants without such fixation regions. Furthermore, it is contemplated that the present implants will be more comfortable to the patient in that they will move more naturally with the body.

In a more specific aspect of the invention, the fixation regions may be located at specific regions on an anterior face of the shell, that is, a face of the shell which faces the front of the human body when the implant has been appropriately implanted in the human body. Alternatively or additionally, one or more discrete fixation surface may be provided on a periphery of the shell (e.g. circumferentially) and/or on the posterior face of the shell, that is, the face of the shell that faces the back of the human body when the implant has been implanted in the human body.

In an even more specific aspect of the invention, the fixation regions comprise at least one elongated region located on the anterior face of the shell. The at least one elongated region may be, for example, a band-shaped region or alternatively, a plurality of band shaped regions having enhanced texture, roughness or sheen.

The elongated fixation regions may be positioned to align with one of the pectoralis major muscle groups or pectoralis minor muscle groups of the human body when the implant is implanted in the body. For example, in one embodiment of the invention, the at least one elongated region comprises a diagonally positioned band shaped region intended to align with the pectoralis major muscle group when the implant has been implanted in the body. In another embodiment, the at least one fixation region comprises a plurality of elongated regions in a radiating configuration generally copying the positioning of the pectoralis minor muscle group wherein the implant has been implanted in the body.

In another broad aspect of the invention, the prosthesis comprises a breast implant having a shell including a fixation region having a first texture and a balance of the shell surface having a second texture that is different from the first texture. In other words, in some embodiments of the invention, the entire, or substantially entire, exterior of the breast implant shell is a textured surface with specific regions thereof having a greater degree of texturing relative to the remaining portions of the textured surface.

It is contemplated that such different texturing will stimulate or encourage different degrees of tissue ingrowth or adhesion at the different fixation regions. For example, in one embodiment, the first fixation region is located on a posterior face of the implant and the second fixation region is located on an anterior face of the implant. The first fixation region may be defined by a texture that is more conducive to tissue interaction and adhesion whereas the second fixation region may be defined by a texture that is relatively less conducive to tissue interaction and adhesion.

In one embodiment, a breast prosthesis is provided having a relatively more significant texture defining the anterior surface of the implant, and a less textured or smooth surface defining the posterior surface of the implant.

In yet another aspect of the invention, the prosthesis comprises a shell having an exterior structured to contact tissue, the shell including a first fixation surface having a first open cell structure, and a second fixation surface having a second open cell structure different than said first open cell structure. In addition, the first fixation surface and the second fixation surface are positioned to encourage respectively different degrees of tissue ingrowth or tissue adhesion by the body at a body-shell interface.

For example, the first open cell structure comprises relatively large open cells and the second open cell structure comprises relatively smaller open cells. Alternatively or additionally, the first open cell structure may comprise a first distribution of cells and the second open cell structure comprises a second distribution of cells wherein the first distribution of cells is relatively more dense than the second distribution of cells.

In yet another specific aspect of the invention, the first open cell structure comprises relatively large rounded open cells and the second open cell structure comprises relatively small rounded open cells. Alternatively, the first open cell structure comprises relatively rounded open cells and the second open cell structure comprises relatively angular open cells.

Advantageously, in accordance with certain embodiments, the first and second fixation surfaces are positioned and structured to be at least somewhat effective to disrupt or disorient capsular tissue formation about the prosthesis after the prosthesis has been implanted in the body.

The present invention further provides a breast prosthesis shell for implantation in a human being, the shell manufactured by the steps of providing a shell precursor; applying a layer of silicone elastomer to the shell precursor, applying solid particles of a first configuration to a portion of the layer of silicone elastomer and applying solid particles of a second configuration to another portion of the layer of silicone elastomer before the layer is fully cured. After the layer including the solid particles embedded therein is cured, the solid particles are then dissolved, for example, by means of a solvent that does not dissolve the silicone elastomer to any appreciable extent. The resulting elastomer shell includes a first open cell texture region formed by said application of the solid particles of the first configuration, and a second open cell texture region formed by said application of the solid particles of the second configuration.

In yet another aspect of the invention, a method of augmenting or reconstructing a breast of a human being is provided. The method generally comprises providing an implantable member including at least one elongated fixation region as described elsewhere herein and implanting the implantable member into a breast of a human being such that the fixation region generally aligns with one of the pectoralis major muscle group and the pectoralis minor muscle group. The method may further comprise filling the implantable member with a liquid or gel prior to or after the implanting step.

In another aspect of the invention, a dual plane breast prosthesis is provided, the prosthesis comprising an implantable member including an exterior defined by a textured lower region or lower pole, configured for subglandular placement, and an upper region or upper pole, that is smooth or differently textured and which is configured for submuscular placement. For example, the first texture and the second texture are structured such that first texture encourages greater tissue ingrowth than the second texture.

In this embodiment, the implant may be surgically positioned as a dual plane breast implant, in other words, the implant may be placed in the breast such that an upper portion of the implant is beneath the pectoralis major muscle, while the lower portion of the implant is in the subglandular plane.

For example, the textured lower region may be a relatively more aggressive textured surface that encourages adhesion and tissue ingrowth, for example, to glandular and fatty tissue, while the upper region may be a less aggressive textured surface, or even a smooth, untextured surface, to allow for more free muscle movement and reduced tissue adhesion.

The textured lower region may encompass between about 20% and about 80% of the surface area of the exterior of the implantable member, or between about 30% and about 70% of the surface area of the exterior of the implantable member, or between about 40% and about 60% of the surface area of the exterior of the implantable member, or about 50% of the surface area of the exterior of the implantable member.

For example, the first texture may comprise an open cell textured surface and the second texture may be a closed cell textured surface. Alternatively, the first texture may comprise a closed cell textured surface and the second texture may be a relatively smooth, untextured surface. Other variations are contemplated.

The present invention further provides methods of augmenting or reconstructing a human breast using a dual plane approach wherein the method comprises implanting in a breast, an implantable member including an exterior defined by a lower surface region encompassing a lower portion of the implantable member and an upper surface region encompassing an upper portion of the implantable member, and wherein the lower surface region is defined by a first textured surface and the upper surface region is defined by one of a smooth surface or a second textured surface different from the first textured surface, and further the implant being placed in the breast such that the upper surface region is positioned between beneath the pectoralis major muscle and the lower region is positioned anteriorly of the pectoralis major muscle.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 1A-1B are a front view and a side elevational view, respectively, of an exemplary round breast implant of the present invention;

FIGS. 2A-2B are a front view and side elevational view, respectively, of an exemplary shaped breast implant of the present invention;

FIGS. 3A and 3B are schematic views of a woman's upper torso showing, alignment of the pectoralis major muscle group and the pectoralis minor muscle group, respectively;

FIGS. 4A, 4B and 4C are vertical sectional views through a woman's breast and adjacent chest anatomy showing, respectively: subglandular, submuscular and dual plane placement of a breast implant of the present invention;

FIG. 7 is a front elevational view of another breast implant in accordance with the invention including a first fixation region having a first texture and a second fixation region having a second texture different from the first texture.

FIGS. 8A and 8B are front and rear elevational views of an exemplary round breast implant of the present invention having a front texture and a rear texture that are different from one another.

FIGS. 10A and 10B show another embodiment of the invention wherein the implant includes a more textured anterior surface and a less textured or smooth posterior surface.

DETAILED DESCRIPTION

Figure 5A:
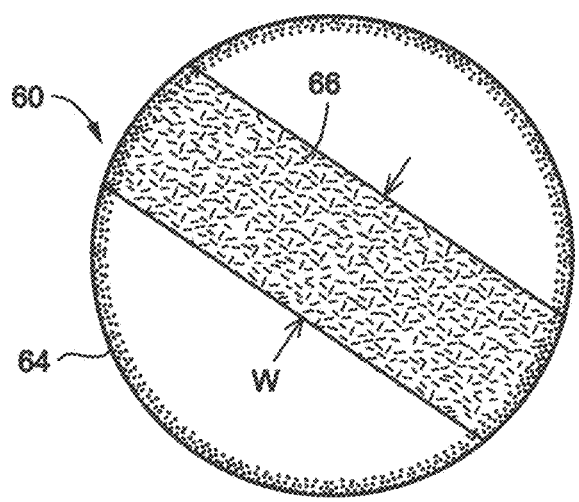
FIGS. 5A-5B are front and side elevational views of an exemplary round breast implant of the present invention having a generally elongated or band-shaped fixation surface.

The present invention provides a saline- or gel-filled soft implant shell, preferably a silicone elastomer shell, with a fixation surface over an exterior portion. The primary application for such soft implants is to reconstruct or augment the female breast. Other potential applications are implants for the buttocks, testes, or calf, among other areas.

The terms "fixation surface" or "fixation region", as used herein, generally refer to a region or portion of an exterior surface of an implant which is positioned, structured or adapted to encourage tissue ingrowth or adhesion at a body/implant interface. For example, a fixation region may be a texture, roughness or sheen that is distinct from, for example, more pronounced than, adjacent surfaces of the implant which do not encourage tissue ingrowth of adhesion to the same degree as the fixation region. For example, other regions or surfaces of the implant exterior may be relatively smooth or less textured relative to the fixation regions.

Such a fixation region may be formed by any suitable means, for example, but not limited to, a salt removal process such as described in U.S. Pat. No. 5,007,929, with appropriate changes being made. Alternatively, the fixation surfaces may be formed by separate textured elements such as textured patches or films adhered to the outside of an otherwise "smooth" or less textured implant. Still, another method for forming the discrete fixation regions may be by using a relatively roughened surface portion of a mold used to form the implant. Another method for forming the present fixation regions includes texturing the exterior of the implant after formation. The present invention should not be considered limited to any particular type of texturing or fixation surface, though there might be certain advantages with one or more of these techniques.

Turning now to the Figures, FIGS. 1A and 1B are front and side elevational views of an exemplary round breast implant 20 of the present invention. Generally, the implant 20 comprises an exterior surface defined by a relatively smooth anterior face 21, a textured posterior face 22 and a textured peripheral region 24 located between the anterior face 21 and the posterior face 22. The relatively smooth anterior face may be a relatively less textured surface (relative to texture of posterior face 22), such as, for example, a fine textured surface or even a matte finish. In some embodiments, the implant 20 has a relatively smooth posterior face, a textured anterior face and a textured or smooth peripheral region. The fixation surfaces 22, 24 themselves may have differing degrees of texturing. The diameter D and front-to-back thickness T of the implant are shown and vary depending on the patient's chest size and aesthetic considerations.

In the shown embodiment, the rear fixation surface 22 extends to the apex 26 or generatrix of the convex outer periphery of the implant 20. The peripheral fixation surface 24 continues forward a short distance S onto the anterior or front surface 21. In some embodiments, the distance S is between about 10% and about 30% of the thickness T. In some embodiments, the peripheral fixation surface 24 extends substantially entirely around the periphery of the implant 20, such that the implant 20 is axi-symmetric. In other embodiments, the peripheral fixation surface 24 may be abbreviated so as to extend around only a portion of the periphery of the implant, such as the inferior or superior half, or the peripheral fixation surface may be broken up into spaced apart segments. In some embodiments, the peripheral fixation surface 24 comprises substantially evenly spaced segments resulting in alternating smooth and textured areas.

FIGS. 2A-2B illustrate an exemplary shaped breast implant 30 of the present invention having an inferior frontal lobe 32 simulating a natural breast. Like implant 20, implant 30 includes a rear fixation surface 34 and a peripheral fixation surface 36. The width W, height H, and front-to-back thickness T of the implant are shown. If the front projection is round, then W=H, otherwise W may be greater than or less than H. When provided with a natural shape, the implant 30 has a proper orientation, namely with the inferior lobe 32 at the lower center. Accordingly, the peripheral fixation surface 36 may extend completely around the periphery of the implant, or may be formed in discrete areas and be oriented relative to the natural shape of the implant. For example, the peripheral fixation surface 36 may be formed only around the inferior or lower half of the implant, or may be formed only on the sides.

FIG. 3A illustrates a woman's upper torso schematically showing on one side placement and alignment of the pectoralis major muscle group, while FIG. 3B illustrates the placement and alignment of the pectoralis minor muscle group. These two muscle groups overlap one another and extend generally from the shoulder or collarbone region to the rib cage underneath the breast. One aspect of the present invention is to provide an implant including fixation surfaces such as described elsewhere herein, which are substantially aligned with these muscle groups when the implant is placed in the body.

While not wishing to be bound by any specific theory of operation, the regions or lines of contact of the implant with the primary chest muscles experience greater movement than other areas of the implant not interfacing the muscles. It is believed by the present inventors that by providing a fixation region of the implant that is substantially coincident with or in substantial alignment with one or more of these muscle groups is more likely to remain secured and move with the muscle. In addition, it is contemplated that such discrete fixation regions may provide the benefit of disrupting capsule formation and/or reducing the potential for capsular contraction.

FIG. 4A is a vertical sectional view through a woman's breast and adjacent chest anatomy showing a subglandular placement of a breast implant 40. The implant 40 is positioned over the top of the pectoralis major muscle group 42, which in turn overlays the pectoralis minor muscle group 44. The chest wall 48 showing a plurality of ribs 50 is also indicated underneath the pectoralis minor muscle 44.

FIG. 4B shows a complete submuscular placement of an implant. In this case, the upper pole, for example, about ⅔ of the upper surface of the breast implant is covered by the pectoralis muscle, and the lower pole, for example, about ⅓ of the lower portion of the breast implant, is covered by the muscle fascia.

FIG. 4C shows a dual plane placement of the implant 40. With a dual plane placement, an upper pole of the implant is partially beneath the pectoralis major muscle, while a lower pole of the implant is located in the subglandular plane. This may be accomplished by creating a pocket beneath the pectoralis major muscle with release of the inferior muscular attachments, with or without partial dissection of the subglandular plane.

Each of these implant placements are utilized primarily depending on the surgeon's clinical determination, sometimes influenced by a dialogue between patient and the surgeon and desired outcome. Depending on the implant placements, the implant 40 may be in contact with one or both muscle groups. In some embodiments of the invention, the implant includes substantially elongated fixation regions as described and shown herein, and said fixation regions being in substantial alignment with the appropriate muscle group which interface the implant when the implant is placed in the body.

Figure 5B:
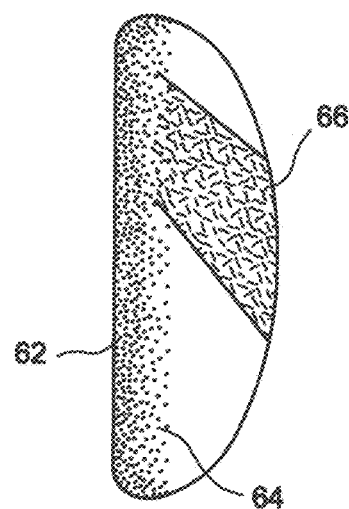

For example, FIGS. 5A-5B are front and side elevational views of an exemplary round breast implant 60 of the present invention having a posterior face 62, a peripheral region 64, and an anterior face including an elongated or band-shaped fixation region 66. The band-shaped fixation region 66 extends generally along a diagonal angle and commences at the front border of the peripheral fixation surface 64. The illustrated embodiment, the fixation region 66 has a substantially constant width W as seen from the front in FIG. 5A. In one embodiment, the width W is between about 1 mm to about 20 mm, for example, between about 2 mm to about 15 mm. Alternatively, although not shown, the fixation region 66 may have a configuration that is other than a constant width.

In one embodiment, the band-shaped fixation surface 66 is generally oriented or aligned with either the pectoralis major muscle group or pectoralis minor muscle group when the implant is implanted in the breast. For instance, if the implant 60 is destined for a submuscular placement such as in FIG. 4B, the fixation surface 66 may be oriented to be generally aligned with the pectoralis major muscle group, as seen in FIG. 3A. Alternatively, the angle at which the insertion surface 66 is oriented may be an approximation of the average angle of the pectoralis major and pectoralis minor muscle groups. In this way, the implant 60 has a fixation surface 66 to encourage tissue ingrowth or adhesion along the major stress lines of the implant. Preferably, the fixation surface 66 is angled between about 30-60° with respect to a vertical plane through the implant 60. Of course, if the implant 60 is round as shown, the fixation surface 66 itself defines the orientation thereof. In one embodiment, the band-shaped fixation surface 66 is centered about the center of the implant 60, therefore creating two symmetric orientations about 180° apart. This arrangement facilitates implant by providing two possible orientations for the surgeon.

The band-shaped fixation region 66 may extend substantially across the anterior face of the implant and may be defined by a texture that is different from a balance of the anterior face. The fixation region 66 may also have a different texture, for example, a more pronounced or more aggressive texture, than the rear fixation surface 62 or peripheral surface 64.

Figure 6A:
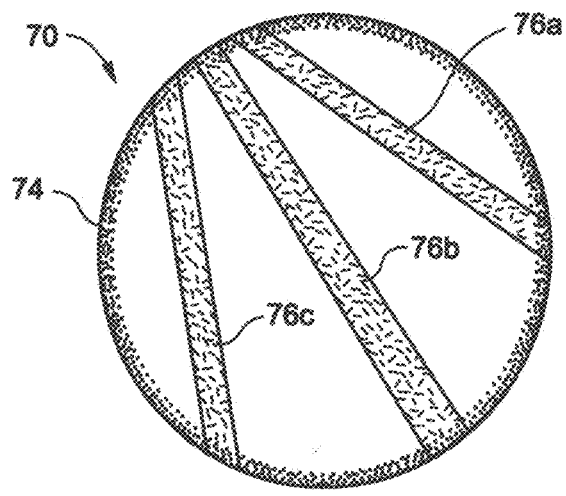
FIGS. 6A-6B are front and side elevational views of an exemplary shaped breast implant of the present invention having a generally elongated or band-shaped fixation surface.
Figure 6B:
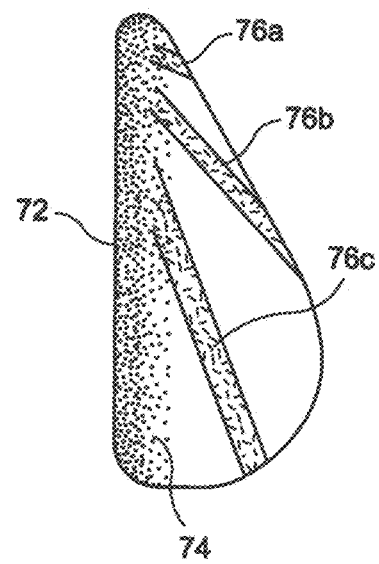

FIGS. 6A-6B illustrate another exemplary shaped breast implant 70 of the present invention. The implant 70 again features a rear fixation surface 72, a peripheral fixation surface 74, and a plurality of separate band-shaped fixation surfaces 76a, 76b, and 76c. These discrete fixation surfaces 76a, 76b, 76c are positioned or configured to align with one or more of the muscle groups described above. For example, the three fixation surfaces 76a, 76b, 76c may be generally oriented relative to the fan-shaped pectoralis minor muscle group. Because the shaped implant 70 is orientation-specific, proper placement of the implant orients the fixation surfaces 76a, 76b, and 76c with the particular muscle group. As mentioned above, the various fixation surfaces 72, 74, 76a, 76b, and 76c may be formed with a similar level of roughness, or some may be less textured, such as with a matte finish. For instance, the rear and peripheral fixation surfaces 72, 74 may have a fine, matte finish, while the frontal fixation surfaces 76a, 76b, 76c are more densely textured. The present invention contemplates all permutations of texturing choices.

In cross-section, the textured implant shells of the present invention may be single- or multi-layered. The overall thickness of the textured implant shell wall may be somewhat greater than a similar smooth-walled shell because of the extra layers of texture.

Turning now to FIG. 7, an anterior (front) view of another breast implant of the present invention is shown generally at 110. The implant 110 includes a shell 112 having an exterior surface including a first fixation region 114 having a first texture 116 and a second fixation region 118 having a second texture 122 that is different from the first texture 116. In the shown embodiment, the first texture 116 is a more "aggressive" texture than the second texture 122. The first texture 116 is structured to encourage a greater degree of tissue interaction than the second texture 122.

In lieu of the second texture 122, it is contemplated that the second fixation region 118, and perhaps the entire balance of the exterior of the shell 112, may be a low sheen surface, for example, a matte finish.

Turning now to FIGS. 8A and 8B, anterior (front) and posterior (rear) views, respectively, of another breast implant in accordance with the invention are shown generally at 210. The implant 210 includes a shell 212 having an anterior face 212a and a posterior face 212b, and including a first fixation region 214 having a first texture 216 and a second fixation region 218 having a second texture 222 that is different from the first texture 216. In the shown embodiment, the first texture 216 may encompass the entire, or substantially entire, anterior face 212a of the implant 210. The first texture 216 is defined by a first distribution of pores, crevices or caverns that is relatively less dense than that of the second texture 222. The second texture 222, which may encompass the entire, or substantially entire, posterior face 221b of the implant 210, may be structured to encourage a greater degree of tissue interaction and adhesion than that of the first texture 216.

The shells 112 and 212 may be manufactured by a method of the invention comprising the steps of providing a shell precursor; applying a layer of silicone elastomer to the shell precursor, applying solid particles of a first configuration to a portion of the layer of silicone elastomer and applying solid particles of a second configuration to another portion of the layer of silicone elastomer before the layer is fully cured. After the layer including the solid particles embedded therein is cured, the solid particles are then dissolved, for example, by means of a solvent that does not dissolve the silicone elastomer to any appreciable extent. The resulting elastomer shell includes a first open cell texture region formed by said application of the solid particles of the first configuration, and a second open cell texture region formed by said application of the solid particles of the second configuration.

One process for forming flexible implant shells for implantable prostheses involves dipping a suitably shaped mandrel into a silicone elastomer dispersion. Many such dispersions are used in the field. Basically they contain a silicone elastomer and a solvent. The silicone elastomer is typically polydimethylsiloxane, polydiphenyl-siloxane or some combination of these two. Typical solvents include xylene or 1,1,1-trichloroethane. Different manufacturers vary the type and amount of the ingredients in the dispersion, the viscosity of the dispersion and the solid content of the dispersion. Nonetheless, the present invention is expected to be adaptable to have utility with a wide variety of silicone rubber dispersions.

The mandrel is withdrawn from the dispersion and the excess silicone elastomer dispersion is allowed to drain from the mandrel. After the excess dispersion has drained from the mandrel at least a portion of the solvent is allowed to volatilize or evaporate. Normally this is accomplished by flowing air over the coated mandrel at a controlled temperature and humidity. Different manufacturers use various quantities, velocities or directions of air flow and set the temperature and humidity of the air at different values. However, the desired result, driving off the solvent, remains the same.

It is also common for prostheses manufacturers to repeat this dip and volatilize procedure a number of times so that a number of layers are built up on the mandrel to reach a desired shell thickness. A layered structure like most current silicone elastomer shells can be made by sequentially dipping the mandrel in different dispersions. Alternatively, the steps may be repeated in a single dispersion so that the finished product is a single homogenous material or layer. That is, the dipping process may be done in multiple stages or steps, each step adding more material, yet the finished product exhibits no distinct layers and the entire shell wall is homogenous or uniform in composition.

An exemplary process for forming the fixation surfaces on either a multi-layered shell or a single-layered shell will now be described. After the mandrel is raised out of the dispersion with what is to be the final layer adhering thereto, this layer is allowed to stabilize. That is, it is held until the final coating no longer flows freely. This occurs as some of the solvent evaporates from the final coating, raising its viscosity.

Again, it should be understood that alternative methods are contemplated for forming the flexible shell prior to the texturing process. The dip molding process advantageously results in the flexible shell pre-mounted on a dipping mandrel, which can then be used for the texturing process. However, if the flexible shell is made by another technique, such as by rotational molding, it can subsequently be mounted on a dipping mandrel and the process continued in the same manner.

Once the flexible shell has been stabilized and mounted on the mandrel, any loose fibers or particles are removed from the exterior of the shell, for example, with an anti-static air gun. A tack coat layer is then applied. The tack coat layer may be sprayed on, but is desirably applied by dipping the flexible shell on the mandrel into a tack coat dispersion. The operator immerses the flexible shell into the dispersion and returns the mandrel to a rack for stabilization. The time required for stabilization typically varies between 5-20 minutes. A suitable tack coat layer is desirably made using the same material employed in the base layers.

At this point, granulated solid particles, for example, dissolvable or leachable particles, are applied over that portion of the exterior surface that will end up as the fixation surface. The solid particles may be applied manually by sprinkling them over the surface while the mandrel is manipulated, or a machine operating like a bead blaster or sand blaster could be used to deliver a steady stream of solid particles at an adequate velocity to the coating on the mandrel. However, a preferred method of solid particle application is to dip the mandrel/shell into a body of the solid particles or expose it to a suspension of the solid particles. It should be understood that the present invention is not intended to be restricted to any one particular method of applying particles. One possible method to apply solid particles to some but not all of the shell is to mask off areas of the shell for which particles are not to be applied and then apply the particles to the non-masked areas.

The tacky flexible shell may then be immersed in a fluidized (air-mixing) aqueous salt bath having regular cubic salt crystals between about 10 to about 600 microns, or round crystals between about 50-2000 microns or a combination thereof. Varying degrees of texturing may be formed with the salt removal process by using differently sized or shaped salt granules (for example, round salt crystals versus angular salt crystals, large salt crystals versus relatively small salt crystals, high density distribution of salt crystals versus relatively low density distribution of salt crystals), on different areas of the shell. The shell is rotated for even coverage, removed, and then allowed to stabilize. After a suitable period of stabilization, such as between about 5-20 minutes, the flexible shells may be dipped into an overcoat dispersion. A suitable overcoat dispersion may be made using the same material employed in the base layers. The flexible shells on the mandrels are then mounted on a rack and allowed to volatilize, such as, for example, about 15 minutes.

The entire silicone elastomer shell structure is vulcanized or cured in an oven at elevated temperatures. The temperature of the oven is preferably kept between about 200° F. and about 350° F. for a curing time preferably between about 20 minutes and about 1 hour, 40 minutes. Upon removal from the oven, the mandrel/shell assembly is placed in a solvent for the solid particles, and the solid particles allowed to dissolve. The solvent does not affect the structure or integrity of the silicone elastomer. When the solid particles have dissolved, the assembly is removed from the solvent and the solvent evaporated. The shell can then be stripped from the mandrel. At this point, it is preferable to place the shell in a solvent for the solid particles and gently agitate it to ensure complete dissolution of all the solid particles. When the shell is removed from the solvent, the solvent is evaporated.

Dissolving the solid particles leaves behind open, interconnected, cavities in the surface of the shell where the salt had been.

After finishing the shell according to the steps described above, the steps required to make a finished breast implant prosthesis may be similar to those known in the art. For example, an opening left by the dip molding process is patched with uncured sheeting, usually made of silicone rubber. Then, if the prosthesis is to be filled with silicone gel, this gel is added and cured, the filled prosthesis packaged, and the packaged prosthesis sterilized. If the prosthesis is to be inflated with a saline solution, a one-way valve is assembled and installed, the prosthesis is post cured if required, and the prosthesis is then cleaned, packaged and sterilized. A combination breast implant prosthesis can also be made wherein a gel-filled sac is positioned inside the shell to be surrounded by saline solution.

In addition to the aforementioned dipping process, the flexible shell for the prosthetic implant may be formed using a molding process. For example, a rotational molding process such as described in Schuessler, U.S. Pat. No. 6,602,452 the entire disclosure of which is incorporated herein, may be used. The process for forming texturing on the exterior surface may be done using a dipping technique after the shell is molded, but another method is to roughen the inside of the mold. For example, a mold having a generally smooth interior surface except for rough areas as described above will produce an implant shell having discrete fixation surfaces. The rotational molding process is advantageous because the entire implant shell may be formed in relatively few manufacturing steps.

Figure 9A:
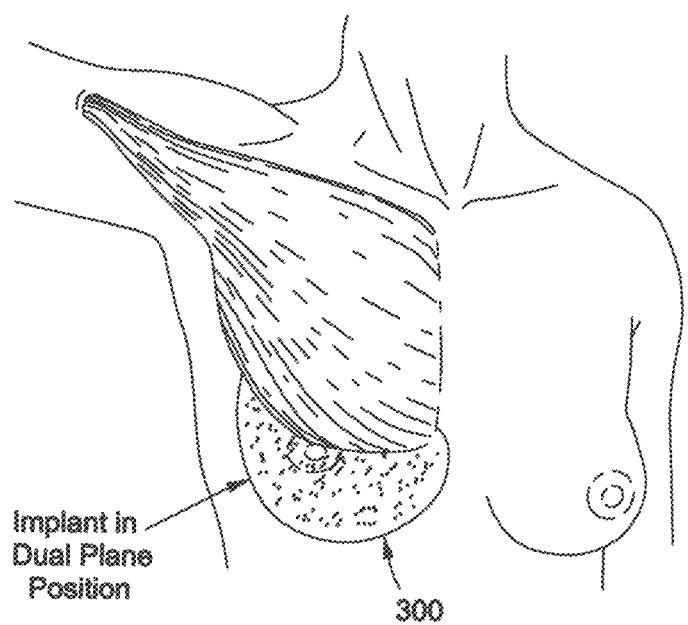
FIG. 9A shows a simplified representation of a dual plane breast implant in accordance with one embodiment of the invention, the implant being shown with an upper region located partially under the pectoralis major muscle and a lower region located in the subglandular plane.
Figure 9B:
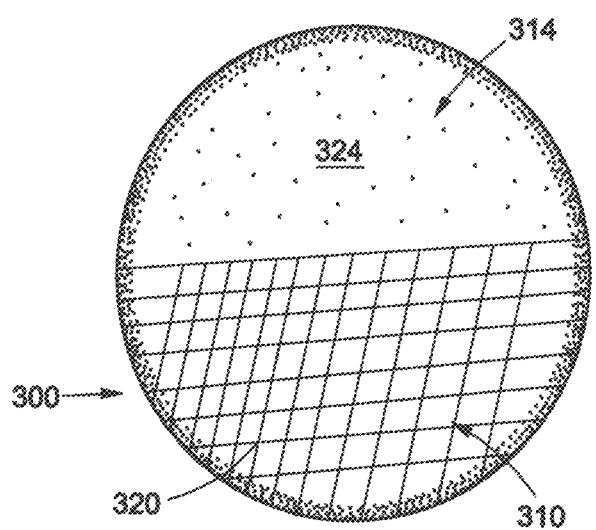
FIGS. 9B and 9C show a front view and side view, respectively, of a dual plane breast implant in accordance with an embodiment of the invention.
Figure 9C:
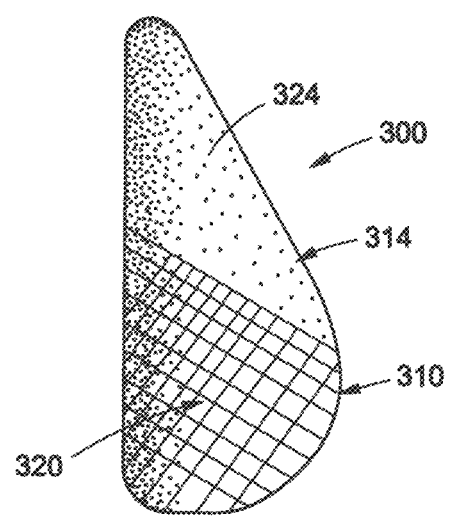

Turning now to FIGS. 9A-9C, another embodiment of the present invention is illustrated, hereinafter sometimes referred to as a "dual plane breast implant." FIG. 9A shows a simplified representation of anatomical placement of such a breast implant 300, and FIGS. 9B and 9C show a front view and side view, respectively, of such an implant 300 in accordance with this embodiment of the invention.

This implant 300 is particularly useful for dual plane breast implant positioning, such as shown in FIG. 4C. In the dual plane placement of breast implants, the upper portion of the implant is covered by muscle while the lower portion of the implant is not. For example, the implant is positioned such that the upper region of the implant is located partially under and interfacing the pectoralis major muscle 400 (see FIG. 9A) and a lower region is located in the subglandular plane and not interfacing muscle tissue.

In one embodiment, the implant 300 generally comprises a relatively textured lower portion 310, e.g. lower pole, and a relatively smooth or less textured upper portion 314, e.g. upper pole. For example, when placed in a "dual plane" position in the breast, the implant 300 of this embodiment invention may have a stronger binding texture 320 on surfaces of the implant 300 that are in contact with glandular tissue (where muscle does not cover/contact the implant 300), and have a less binding surface 324 on surfaces of the implant 300 in contact with muscle tissue. Although an anatomical, or "teardrop" shaped implant is shown in FIGS. 9A and 9B, it should be appreciated that this dual plane embodiment may comprises other shapes, for example, a "round" shaped implant, such as shown in FIGS. 1A and 1B.

The lower portion 310 of the exterior surface of the implant 300 may have an open-cell textured surface which is designed or structured to provide enhanced tissue ingrowth and adhesion. The upper portion 312 of the exterior surface of the implant may have a smooth surface, a closed cell textured surface, or another surface configuration that is relatively less aggressive/less conducive to tissue adhesion and ingrowth than the texture on the lower portion 310. Many varieties and permutations are contemplated and are considered to fall within the scope of the invention.

One advantage of this embodiment 300 is that strong tissue adherence would not be directly associated with attachment to muscle tissue which may be more difficult to separate from a strong binding texture. In addition, a weak or non-binding surface under the muscle may allow the muscle to slide on the surface of the implant and reduce the tension on the implant or the movement of the implant with each flexing of the muscle. This embodiment may be particularly advantageous in athletic woman because it may enhance comfort and the ability to move the muscles of the chest wall while enabling the implant to remain fixed and anchored in the glandular tissue.

In another embodiment of the invention shown in FIGS. 10A and 10B, an implant 400 is provided having a more aggressive texture 412 for strong tissue binding or integration on the anterior surface of the implant 400, and therefore fixation of the implant on the anterior portion of the implant, and a smooth surface or less textured surface 414 resulting in reduced fixation on the posterior portion of the implant 400. One advantage of this approach is that should the implant 400 need to be removed, the portion of the implant 400 facing the rib cage can be more easily released from the tissue and reduce the potential risks of surgical separation of the implant from the tissue in proximity to the ribs and plural cavity. Another advantage is that the smooth or less textured posterior side of the implant would allow for some movement or sliding of the implant 400, thereby reducing strain on the implant itself when the implant is placed submuscularly or in a dual plane position where constant flexing of the muscle would potentially continually exert pressure on the implant. This approach would be applicable to both smooth and shaped implants and would reduce the potential for rotation. It would also have the added benefit of potentially reducing contracture since the texture would still provide a disruption of the alignment of the collagen fibers in any developing capsule.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A breast implant prosthesis comprising an exterior having a posterior surface, an anterior surface, an upper portion, and a lower portion, the prosthesis having (i) a lower pole region with a textured outer surface that forms a fixation region configured for subglandular placement and (ii) an upper pole region with a smooth outer surface configured for submuscular placement, a boundary between the fixation region and the upper pole region extending transverse relative to a vertical axis of the implant prosthesis when seen in side view, the textured outer surface of the lower pole region extending along only the lower portion of the exterior, the smooth outer surface of the upper pole region extending along the upper portion of the exterior along at least one of the posterior surface or the anterior surface of the exterior, the smooth outer surface of the upper pole region having a texture different from the textured outer surface of the lower pole region.

2. The prosthesis of claim 1, wherein the textured outer surface of the lower pole region encompasses between about 20% and about 80% of the exterior.

3. The prosthesis of claim 1, wherein the textured outer surface of the lower pole region encompasses between about 30% and about 70% of the exterior.

4. The prosthesis of claim 1, wherein the textured outer surface of the lower pole region encompasses between about 40% and about 60% of the exterior.

5. The prosthesis of claim 1, wherein the textured outer surface of the lower pole region encompasses about 50% of the exterior.

6. The prosthesis of claim 1, wherein the textured outer surface of the lower pole region extends along the posterior surface.

7. The prosthesis of claim 6, wherein the textured outer surface of the lower pole region further extends along the anterior surface.

8. The prosthesis of claim 1, wherein the textured outer surface of the lower pole region extends along the anterior surface.

9. The prosthesis of claim 1, wherein the smooth outer surface of the upper pole region extends along the posterior surface.

10. The prosthesis of claim 9, wherein the smooth outer surface of the upper pole region extends along the anterior surface.

11. The prosthesis of claim 1, wherein the textured outer surface of the lower pole region outer surface comprises a plurality of textured bands.

12. The prosthesis of claim 1, wherein the textured outer surface of the lower pole region outer surface comprises a plurality of textured bands extending along an anterior.

13. A method of augmenting or reconstructing a human breast comprising: implanting in a breast a breast implant including an exterior having a posterior surface, an anterior surface, an upper portion, and a lower portion, the breast implant having (i) lower pole region with a textured outer surface that forms a fixation region and (i) upper pole region with a smooth outer surface, the fixation region having an upper edge extending at an angle relative to a vertical axis of the implant, the textured outer surface of the lower pole region extending along only the lower portion of the exterior, the smooth outer surface of the upper pole region extending along the upper portion of the exterior along at least one of the posterior surface or the anterior surface of the exterior, the breast implant being positioned such that the textured outer surface of the lower pole region is placed subglandularly and the smooth outer surface of the upper pole region is placed submuscularly.

14. The method of claim 13, wherein the textured outer surface of the lower pole region encompasses between about 20% and about 80% of the exterior.

15. The method of claim 13, wherein the textured outer surface of the lower pole region encompasses between about 30% and about 70% of the exterior.

16. The method of claim 13, wherein the textured outer surface of the lower pole region encompasses between about 40% and about 60% of the exterior.

17. The method of claim 13, wherein the textured outer surface of the lower pole region comprises a plurality of textured bands.

18. The method of claim 13, wherein the textured outer surface of the lower pole region comprises a plurality of textured bands encompassing between about 20% and about 80% of the exterior.

19. The method of claim 13, wherein the textured outer surface of the lower pole region comprises a plurality of textured bands encompassing between about 30% and about 70% of the exterior.

20. The method of claim 13, wherein the textured outer surface of the lower pole region comprises a plurality of textured bands encompassing between about 40% and about 60% of the exterior.

* * * * *

UNITED STATES PATENT AND TRADEMARK OFFICE
CERTIFICATE OF CORRECTION

Page 1 of 1

PATENT NO. : 10,765,501 B2
APPLICATION NO. : 15/819544
DATED : September 8, 2020
INVENTOR(S) : Dennis E. Van Epps et al.

It is certified that error appears in the above-identified patent and that said Letters Patent is hereby corrected as shown below:

In the Claims

In Column 14, Line 22, in Claim 13, delete "(i)" and insert -- (ii) --, therefor.

Signed and Sealed this
Tenth Day of November, 2020

Andrei Iancu
*Director of the United States Patent and Trademark Office*